United States Patent [19]

Haan

[11] Patent Number: 4,559,049
[45] Date of Patent: Dec. 17, 1985

[54] URINAL WITH A CHECK VALVE ON A FLACCID DRAIN LINE

[76] Inventor: Wilhelmus A. O. Haan, Bazuinlaan 7, 5402 PB Uden, Netherlands

[21] Appl. No.: 674,363

[22] Filed: Nov. 23, 1984

Related U.S. Application Data

[63] Continuation of Ser. No. 268,982, May 8, 1981, abandoned.

[51] Int. Cl.⁴ ............................................. A61F 5/44
[52] U.S. Cl. ................................... 604/350; 604/323
[58] Field of Search ............. 417/478; 604/349–353, 604/153, 282, 323, 335; 138/118, 119, 128, 170, DIG. 7

[56] References Cited

U.S. PATENT DOCUMENTS

| | | | |
|---|---|---|---|
| 2,382,276 | 8/1945 | Wells | 4/110 |
| 2,583,069 | 1/1952 | Votruba | 120/1.41 |
| 2,745,111 | 5/1956 | Podmorski | 604/350 |
| 3,191,600 | 6/1965 | Everett | 604/323 |
| 3,295,556 | 1/1967 | Gertsima et al. | 138/128 |
| 3,298,370 | 1/1967 | Beatty | 604/350 |
| 3,306,296 | 2/1967 | Moss | 604/347 |
| 3,421,507 | 1/1969 | Gresham | 604/349 |
| 3,823,716 | 7/1974 | Hale | 604/335 |
| 3,835,857 | 9/1974 | Rogers et al. | 604/34 |
| 4,020,843 | 5/1977 | Kanall | 604/351 |
| 4,022,213 | 5/1977 | Stein | 604/350 |
| 4,119,128 | 10/1978 | Bishop | 150/8 |
| 4,257,422 | 3/1981 | Duncan | 604/282 |
| 4,360,042 | 11/1982 | Fouss | 138/105 |

FOREIGN PATENT DOCUMENTS

| | | | |
|---|---|---|---|
| 25708 | 1/1972 | Australia . | |
| 2279425 | 2/1976 | France | 604/349 |
| 55267 | 5/1977 | Japan | 138/118 |
| 5863 | of 1897 | United Kingdom | 138/170 |

Primary Examiner—C. Fred Rosenbaum
Assistant Examiner—J. L. Kruter
Attorney, Agent, or Firm—Diller, Ramik & Wight

[57] ABSTRACT

A device for collecting urine from an incontinent patient includes two synthetic resin foils having enlarged portions and narrow, neck-like portions projecting therefrom. These foils are registered in superimposed relation and sealed around the enlarged portions and along the edges of the neck-like portions to define a flexible receptacle for urine between the enlarged portions and a duct between the neck-like portions. A one way valve and an external catheter are in fluid connection with one end of the duct and through the duct with the receptacle. The device is attached to the patient's leg and the inner wall of the duct in contact with the user's leg is of smaller width than the outer wall of the duct so that the outer wall is in flaccid, collapsed condition against the inner wall but may flex away from the inner wall to define a passage for urine into the receptacle.

1 Claim, 4 Drawing Figures

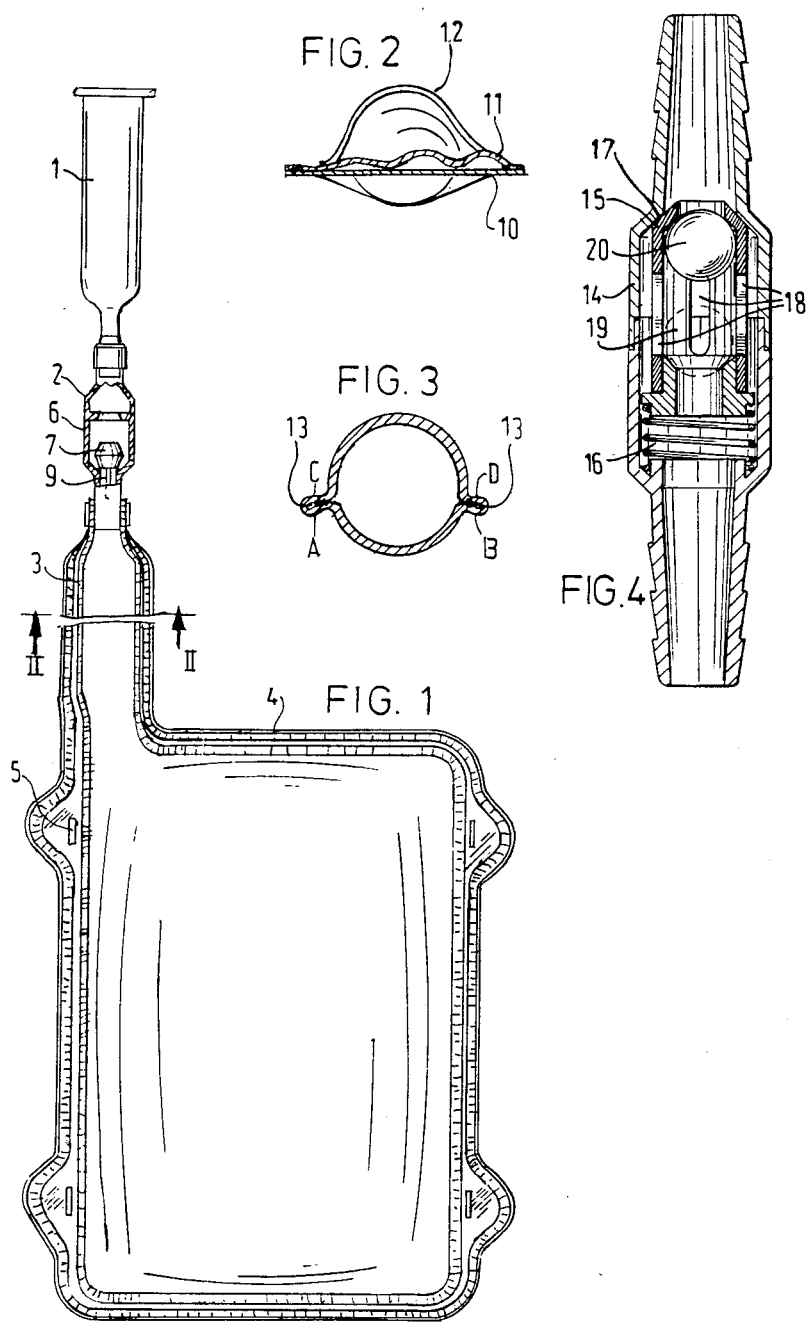

URINAL WITH A CHECK VALVE ON A FLACCID DRAIN LINE

This application is a continuation, of application Ser. No. 268,982, filed May 8, 1981 now abandoned.

The invention relates to a device for collecting urine of incontinent patients, said device comprising an internal or external catheter and a duct connected herewith and leading to a receptacle.

The invention has for its object to provide a device of the kind set forth, in which the user has optimum freedom of movement, and can readily exchange the urinal and infections of the urethra of the user are minimized.

The device according to the invention is distinguished in that the duct is made from light, deformable material, the duct having in the direction of length at least two rib-shaped wall reinforcements so that the width of the wall portion between the two stiffening ribs is unequal to the width of the opposite wall portion between said two stiffening ribs.

Owing to such a shape of the outlet duct for the urine the fluid can always be conducted away to the receptacle, whilst the flexible duct readily matches the shape of the body and the movements of the user.

Preferably the receptacle is also made from flexible material, whilst in accordance with the invention a non-return valve is arranged downstream of the catheter. This non-return valve serves to retain fluid tending to flow back to the catheter when the receptacle is deformed by a movement of the user. The shape of the duct proposed by the invention will not prevent a backward flow of the fluid so that a quick-action non-return valve is required.

The valve body is preferably constructed in the form of a float or in other terms it is made from a material having a specific weight of less than 1. When fluid flows back the valve body will float with the fluid and clog the passage.

According to the invention, in order to render the non-return valve suitable for a dropwise evacuation of urine as well as for the discharge of a larger quantity at a time the valve housing is provided with a second, spring-loaded valve body. This spring-loaded valve body opens when a large amount of fluid has to be conducted away, whilst the opening to be closed by the float is suitable for continuous, dropwise evacuation of the fluid.

In a preferred embodiment the floating body is arranged in an uninterrupted bore of a second non-return valve body so that a compact non-return valve is obtained, which will hinder the user as little as possible.

According to the invention the duct and the receptacle are made integrally from synthetic resin foil. In this way a so-called "disposable" is obtained.

The invention furthermore relates to a method of manufacturing such an integral unit of duct and receptacle, said method being distinguished in that parts of synthetic foil of equal shape are laid down on the other, the edges of said two parts foil are welded to one another and one of the parts is thermally shrunk. In this manner a very cheap disposable is obtained and at the same time the duct proposed by the invention is obtained in which the welded strips form the stiffening edges for keeping the duct open at all time.

The invention will be described more fully with reference to a drawing in which:

FIG. 1 is an elevational view of a urinal in accordance with the invention,

FIGS. 2 and 3 cross-sectional views of different embodiments of the duct to be used with the urinal of FIG. 1 and FIG. 4 shows an alternative embodiment of the non-return valve in a longitudinal sectional view.

Referring to FIG. 1, reference numeral 3 designate an external catheter for an incontinent male patient, with which catheter is connected the valve housing of a non-return valve 2. With the opposite side of the valve housing is connected a duct 3 with a receptacle 4. The receptacle is provided with eyelets 5 for the connection of fastening means so that the receptacle 4 can be fastened around the patient's leg.

The non-return valve 2 comprises a housing 6 of, for example, synthetic material which may be formed by spray-casting. The housing contains a floating body 7, for example, of synthetic foam having such a specific weight that when fluid flows towards the catheter 1 from the receptacle 4, the floating body 7 floating on the fluid immediately closes the passage 8 of the housing 6. The floating body 7 has the shape of barrel, the frustoconical top of which co-operates with the opening 8, whereas the frustoconical bottom terminates in a prolongation 9 of cross-shaped section accomodated in the bore of the lower connecting stub of the housing 6. The prolongation 9 ensures that the floating body 7 remains in the correct position relative to the housing 6.

FIGS. 2 and 3 show different structures of the duct 3 in cross-sectional view. The duct shown in FIG. 2 is formed by two synthetic foil portions 10 and 11, the peripheral strips of which are welded together. After thermal shrinkage of portion 10 portion 11 witll invariably exhibit the shape of a placed wave in the straight position of portion 10 so that when lying flat on the patient's skin the duct will always have a passage. This ensures a disturbance-free evacuation of the fluid. In a similar manner the receptacle 4 may be manufactured and in accordance with the invention the duct 3 and the receptacle 4 may be integrally made from synthetic resin foil so that this part of the urinal constitutes a disposable.

The synthetic foil has such a flexibility that even when a large amount of urine is conducted away that duct 3 can readily expand to the form indicated by line 12 in FIG. 2.

FIG. 3 shows a different embodiment of the duct for which likewise flexible synthetic resin may be used, which is directly extruded in the form of a hose. The wall may be stiffened at two places by folding the wall outwardly and welding the parts to one another or by adhering them in a different, suitable manner at 13. According to the invention the places 13 have to be such that the distance A-B along the lower side between the places 13 differs from the distance C-D along the top side of the hose periphery.

FIG. 4 is a cross-sectional view of the non-return valve suitable for use in the urinal shown in FIG. 1.

The valve comprises in this case a housing 14 provided on both sides with connecting stubs for the duct 3 and the catheter 1 respectively. The housing 14 contains a spring-loaded valve body 15, which is held by the compression spring 16 on the valve seat 17. On the side remote from the valve body 15 the spring 16 is supported in the valve housing 14. The valve body 15 has an uninterrupted bore 19 accomodating a float 20 in the form of a ball. Openings 18 establish a communication between the bore 19 and the space around the valve body 15.

This embodiment of the non-return valve shown in FIG. 4 is extremely suitable for evacuating a large quantity of liquid, in which case the valve body 15 is lifted from the seat 17 against the action of the spring 16 so that a large passage is formed, whereas in the case of dropwise secretion of the incontinent patient the liquid can flow away undisturbed via the uninterrupted bore 19 in the valve body 15. In the event of an abrupt reflux of the urine the float 20 will immediately shut the uninterrupted bore 19 on the top side of the valve body 15, whilst the valve body 15 is permanently urged against the seat 17.

The invention is not limited to the embodiments described above.

What is claimed is:

1. A device for collecting urine from incontinent patients, comprising the combination of:

a first layer of flexible synthetic resin foil and a second layer of synthetic resin foil, said layers each having an enlarged portion and a narrow, neck-like portion projection therefrom, said layers being disposed in superimposed and generally registered relation;

means for joining said layers substantially circumferentially around said enlarged portions and along opposite sides of said narrow, neck-like portions to form a flexible receptacle for urine between said enlarged portions, to form a flexible duct means between said narrow, neck-like portions, to form an inlet mouth at the juncture of said flexible duct means and said flexible receptacle, and to form an inlet opening at that end of the duct means remote from said inlet mouth;

said flexible receptacle for urine being adapted to be affixed to a patient's leg;

said flexible duct means leading from said inlet opening to said inlet mouth, said duct means comprising an inner wall adapted to contact the patient's leg and an outer wall overlying said inner wall, said inner wall being adapted to contact the patient's leg and having a width less than the width of said outer wall which is in a flaccid, collapsed condition against said inner wall so that urine passes through the duct means said outer wall will flex outwardly to a transient condition out of contact with said inner wall from the collapsed condition to define a passage to allow urine to flow therethrough to the flexible receptacle;

a one way valve connected to that end of said duct means defining said inlet opening; and an external catheter for directing the patient's urine into said passage through said one way valve;

said one way valve being in fluid connection between said external catheter and said inlet opening of the duct means.

* * * * *